US009717239B2

(12) United States Patent
Sun et al.

(10) Patent No.: US 9,717,239 B2
(45) Date of Patent: Aug. 1, 2017

(54) CELLULOSE ETHER AS A DRIFT CONTROL AGENT AND RAINFASTNESS AGENT

(71) Applicant: Akzo Nobel Chemicals International B.V., Amersfoort (NL)

(72) Inventors: Jinxia Susan Sun, Hopewell Junction, NY (US); Qiwei He, Belle Mead, NJ (US); Shawn Zhu, Stormville, NY (US); Logan Dempsey, Princeton, NJ (US); Michael Walters, Rhinebeck, NY (US); Peter Westbye, Stenungsund (SE)

(73) Assignee: AKZO NOBEL CHEMICALS INTERNATIONAL B.V., Arnhem (NL)

( * ) Notice: Subject to any disclaimer, the term of this patent is extended or adjusted under 35 U.S.C. 154(b) by 0 days.

(21) Appl. No.: 14/773,423

(22) PCT Filed: Mar. 11, 2014

(86) PCT No.: PCT/EP2014/054628
§ 371 (c)(1),
(2) Date: Sep. 8, 2015

(87) PCT Pub. No.: WO2014/139975
PCT Pub. Date: Sep. 18, 2014

(65) Prior Publication Data
US 2016/0015027 A1    Jan. 21, 2016

Related U.S. Application Data

(60) Provisional application No. 61/783,871, filed on Mar. 14, 2013.

(30) Foreign Application Priority Data

Jul. 4, 2013   (EP) .................................. 13175101

(51) Int. Cl.
| A01N 25/02 | (2006.01) |
| A01N 25/24 | (2006.01) |
| A01N 39/04 | (2006.01) |
| A01N 57/20 | (2006.01) |

(52) U.S. Cl.
CPC ............. *A01N 25/24* (2013.01); *A01N 25/02* (2013.01); *A01N 39/04* (2013.01); *A01N 57/20* (2013.01)

(58) Field of Classification Search
CPC ................................ A01N 25/02; A01N 25/24
See application file for complete search history.

(56) References Cited

U.S. PATENT DOCUMENTS

| 4,644,063 A | 2/1987 | Masaki et al. |
| 7,319,146 B2 * | 1/2008 | Bostrom ............... C08B 11/193 536/85 |
| 7,504,498 B2 | 3/2009 | Berglund et al. |
| 8,093,184 B2 * | 1/2012 | Kawanaka ............ A01N 25/04 504/128 |
| 2004/0268428 A1 | 12/2004 | Duzan, Jr. et al. |
| 2006/0075921 A1 | 4/2006 | Richardson et al. |
| 2008/0286223 A1 | 11/2008 | Fuls et al. |
| 2009/0247407 A1 | 10/2009 | Kravets et al. |

FOREIGN PATENT DOCUMENTS

| CN | 101396018 A | 4/2009 |
| CN | 101433202 A | 5/2009 |
| CN | 102187861 A | 9/2011 |
| CN | 102283194 A | 12/2011 |
| CN | 102301997 A | 1/2012 |
| CN | 102342292 A | 2/2012 |
| CN | 102505878 A | 6/2012 |
| RU | 2 097 960 C1 | 12/1997 |
| SU | 1340619 A1 | 9/1987 |
| SU | 1436907 A1 | 11/1988 |
| WO | 2007/034250 A1 | 3/2007 |
| WO | 2012/080196 A2 | 6/2012 |

OTHER PUBLICATIONS

International Search Report and Written Opinion of International Application No. PCT/EP2014/054628, mailed Apr. 15, 2014.
Search Report of EP Application No. 13175101.8, dated Sep. 19, 2013.
Anna et al., "Elasto-capillary thinning and breakup of model elastic liquids," Department of Chemical Engineering, Carnegie Institute of Technology, The Society of Rheology, Inc. (2001), pp. 115-138.
Christanti et al., "Surface tension driven jet break up of strain-hardening polymer solutions," Department of Chemical Engineering, Center for Complex Fluids Engineering, Carnegie Mellon University, Journal of Non-Newtonian Fluid Mechanics 100, (2001), pp. 9-26.
Mei Li et al., "Enlist Duo Herbicide: A Novel 2,4-D Plus Glyphosate Premix Formulation with Low Potential for Off-target Movement," (2011), ASTM International, pp. 3-15.
Rodd et al., "Capillary Break-Up Rheometry of Low-Viscosity Elastic Fluids," Appled Rheology vol. 15 Issue 1 (2005), pp. 12-27.
Tirtaatmadja et al., "Drop formation and breakup of low viscosity elastic fluids: Effects of molecular weight and concentration," Physics of Fluids 18, 043101 (2006), American Institute of Physics.

* cited by examiner

*Primary Examiner* — Michael B Pallay
(74) *Attorney, Agent, or Firm* — Matthew D. Kellam

(57) ABSTRACT

Disclosed is an agricultural composition comprising at least one agricultural chemical and at least one cellulose ether, wherein the cellulose ether is a nonionic methylethylhydroxyethyl cellulose (MEHEC) polymer as well as a method for reducing spray drift during the spraying of an aqueous solution. The method comprises combining the MEHEC polymer with at least one agricultural chemical to obtain the aqueous solution and spraying the aqueous solution. Also disclosed is a method for increasing resistance to rain wash off of an aqueous solution sprayed onto a surface.

7 Claims, 1 Drawing Sheet

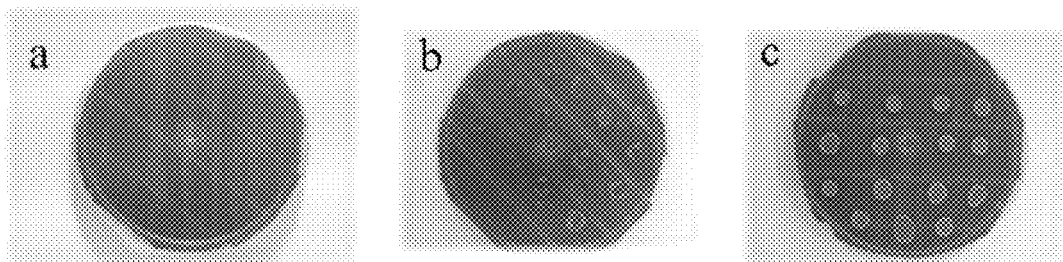

CELLULOSE ETHER AS A DRIFT CONTROL AGENT AND RAINFASTNESS AGENT

This application is a national stage filing under 35 U.S.C. §371 of PCT/EP2014/054628, filed Mar. 11, 2014, which claims priority to U.S. Provisional Patent Application No. 61/783,871, filed Mar. 14, 2013, and European Patent Application No. 13175101.8, filed Jul. 4, 2013, the contents of which are each incorporated herein by reference in their entireties.

FIELD OF THE INVENTION

The present invention relates to a novel cellulose ether capable of reducing spray drift during the spraying of an aqueous solution containing such cellulose ether and capable of resisting rain wash-off.

BACKGROUND OF INVENTION

The fine droplets in the spray mist generated during spraying of a pesticide formulation can travel with the wind, hence exposing human, wildlife, and the environment to pesticide residues that may have health and environmental effects and may cause property damage.

Various methods have been proposed in an attempt to reduce the amount of drifting of fine droplets during spraying of an aqueous pesticide solution. One method is to modify the nozzle design so as to allow bigger spray droplets when the liquid passes through of the nozzle. Another method is to use a drift control chemical agent. Various drift control agents are known, including polymers and surfactants. One useful polymer class is a high molecular weight water soluble polysaccharides such as derivatives of guar gum and xanthan gum. It has been generally accepted that the mechanism of drift control by polymers is that these polymers increase the elongational (or extensional) or kinematic (or intrinsic) viscosity of the diluted aqueous solution to, for example above 6 dl/g. The increased viscosity usually results in increased droplet size and reduced fines. Over the years, researchers have found that the optimum spray pattern has a droplet size distribution in the mist between 150-400 µm. Guar gum derivatives are efficient drift control agents. They can reduce the fine droplets dramatically even at a very low concentration such as ~<0.06 wt.

Cellulose is a polysaccharide built up from 1,4-anhydroglucose units. The cellulose molecules in native cellulose are insoluble in water. To make cellulose soluble, it has to be modified into a cellulose derivative, such as hydroxyethyl cellulose (HEC), ethyl hydroxyethyl cellulose (EHEC), hydroxylpropyl cellulose (HPC), hydroxybutyl methylcellulose (HBMC), hydroxypropyl methylcellulose (HPMC), methyl ethyl hydroxyethyl cellulose (MEHEC), and hydrophobically modified ethyl hydroxyethyl cellulose (HMEHEC).

The use of some cellulose derivatives as drift control agents has been known. While there is a preference for cellulosic derivatives over guar and xanthan gum due to their abundance and renewable property, these cellulose derivatives have marginal drift control property.

SUMMARY OF THE INVENTION

It has been unexpectedly discovered that nonionic methylethylhydroxyethyl cellulose (MEHEC), when present in an aqueous spray medium at very low concentration, can reduce the fine spray droplets below 150 µm effectively. In addition, the drift control property of such novel cellulose ether is insensitive to prolonged shearing in a typical agricultural spraying practice. Moreover, it has also been unexpectedly discovered that the MEHEC possesses an excellent rainfastness property, i.e., the property to resist wash-off of sprayed pesticides on plant surface (e.g., leaf) by rain shortly after spraying.

To date, there has been no teaching or disclosure on the use of MEHEC as a drift control agent or as a rainfastness agent. As mentioned above, the use of some cellulose derivatives as drift control agents has been known; however, they have marginal drift control property. As unexpectedly discovered by the present inventors, MEHEC can function as a good rainfastness agent as well as a good drift control agent.

Accordingly, the present invention is directed to an agricultural composition comprising at least one agricultural chemical and at least one cellulose ether, wherein the cellulose ether is a nonionic MEHEC polymer. The present invention is also directed to a method for reducing spray drift during the spraying of an aqueous solution. The method comprises: providing a nonionic MEHEC polymer; combining the MEHEC polymer with at least one agricultural chemical to obtain the aqueous solution; and spraying the aqueous solution. Further, the present invention is also directed to a method for increasing resistance to rain wash off of an aqueous solution sprayed onto a surface. The method comprises: providing a nonionic MEHEC polymer; combining the MEHEC polymer with at least one agricultural chemical to obtain the aqueous solution; and spraying the aqueous solution onto the surface.

BRIEF DISCUSSION OF DRAWINGS

The FIGURE is a picture showing the results of rainfastness comparing a control composition without a rainfastness agent, a composition with guar gum, and a composition with MEHEC according to the present invention.

DETAILED DESCRIPTION OF THE INVENTION

The present invention is directed to an agricultural composition comprising at least one agricultural chemical and at least one cellulose ether, wherein the cellulose ether is a nonionic MEHEC polymer. The present invention is also directed to a method for reducing spray drift during the spraying of an aqueous solution. The method comprises: providing a nonionic MEHEC polymer; combining the MEHEC polymer with at least one agricultural chemical to obtain the aqueous solution; and spraying the aqueous solution. Further, the present invention is also directed to a method for increasing resistance to rain wash off of an aqueous solution sprayed onto a surface. The method comprises: providing a nonionic MEHEC polymer; combining the MEHEC polymer with at least one agricultural chemical to obtain the aqueous solution; and spraying the aqueous solution onto the surface.

An illustrative structure of MEHEC is shown below:

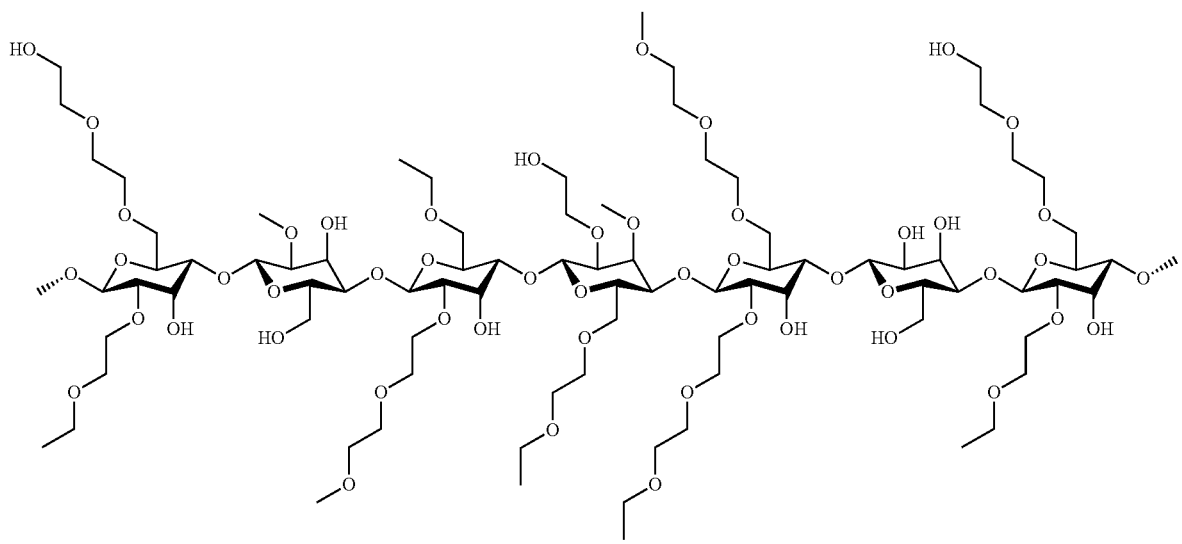

In another aspect of the invention, the MEHEC polymer has a degree of substitution of greater than about 0.3 for methyl ($DS_M$); in one embodiment, greater than about 0.4; in another embodiment, greater than about 0.5. In another aspect of the invention, the MEHEC polymer has a degree of substitution of greater than about 0.2 for ethyl ($DS_{ET}$); in one embodiment, greater than about 0.3. In another aspect of the invention, the MEHEC polymer has an average molar substitution of ethylene oxide group on each sugar unit ($MS_{EO}$) of greater than about 0.8; in one embodiment, greater than about 1. It is noted that the determination of the degree of substitution and average molar substitution is well known in the art and one skilled in the art is familiar therewith.

In another aspect of the invention, the MEHEC polymer has a viscosity of greater than 5,000 cps measured at 1% concentration in water at pH=7 using a Brookfield viscometer type VI at 12 rpm using spindle number 3 at 20 degree C. in a container with diameter of 6.5 cm. In one embodiment, the MEHEC polymer has a viscosity of greater than 7,000 cps; in another embodiment, greater than 8,000 cps.

In one embodiment, the agricultural composition comprises 0.01-0.5 wt % of the MEHEC polymer and more than about 50 wt % of water. In another embodiment, the agricultural composition comprises 0.02-0.3 wt % of the MEHEC polymer; in yet another embodiment, 0.03-0.2 wt % of the MEHEC polymer, in yet another embodiment, 0.05-0.125 wt % of the MEHEC polymer. In another embodiment, the agricultural composition comprises more than about 80 wt % of water; in yet another embodiment, more than about 95 wt % of water, in yet another embodiment, more than about 98% of water.

The MEHEC polymer may be in a powder form. The MEHEC polymer may also contain certain process aids such as an anti-caking agent, a wetting agent, and/or a flowing aid. Additionally, the MEHEC polymer may be made into a liquid form by suspending or dissolving it into a medium. The MEHEC polymer may also be used together with other drift control agents, including guar gum.

In one aspect of the invention, the agricultural composition is substantially free of aluminosilicate mineral, more specifically, foamed aluminosilicate mineral. In another aspect of the invention, the composition is not in a form of or is substantially free of granules with pores.

"Substantially free of" a certain component for the purpose of the present invention means that the content of such certain component in the composition is less than 10 wt %, more specifically less than 5 wt %, even more specifically less than 1 wt %, in particular less 0.5 wt %, and even more particular less than 0.1 wt %.

The agricultural chemical according to the present invention may include pesticides, growth regulators, micronutrients, and/or fertilizers. The pesticides may include herbicides, insecticides and/or fungicides known in the art. More specifically, the insecticide may be selected from the group consisting of chlofenapyr, pyrethrin, piperonyl butoxide and mixtures thereof. As to the herbicide, it may be selected from the group consisting of glyphosate, 2,4-D, sulfonyl urea, dicamba, and mixtures thereof; and as to the fungicide, it may be selected from the group consisting of sulfur, dithiocarbamates and their derivatives, nitro derivatives, heterocyclic substances, strobilurins, anilinopyrimidines, and mixtures thereof.

The agricultural composition according to the present invention may further comprise at least one surfactant. Examples of surfactants suitable for use in the present invention include, but are not limited to, nonionic surfactants such as alcohol alkoxylates, alkylphenol alkoxylates, fatty acid alkoxylates, alkyl polyglucosides, and alkoxylated methylated seed oils); anionic surfactants such as alkyl sulfates, alkyl ethersulfates, sulfonates including alkyl benzene sulfonates, and phosphate esters; and nitrogen containing surfactants such as alkanol amides and their alkoxylates, alkylamines and their alkoxylates, alkylamine quaternary surfactants, alkoxylated alkylamine quaternary surfactants, alkyl dimethyl betaines, alkyl dimethyl amine oxide, alkoxylated alkyl amine oxide, amidoamines derived from fatty acid and diethylenetriamine, dimethylamidopropylamine, ethylene diamines and their oxides, betaine, and quaternary, alkoxylated amidoamine and their amine oxide, betaines, and quaternary. More particularly, the surfactant may be selected from the group consisting of a dialkyl (C12-C22) quaternary surfactant, an alkyl (C12-C22) dimethylbetaine, an alkyl (C12-C22) dimethylamine oxide, an ethoxylated alkyl (C12-C22) amine oxide with less than 4EO units, an ethoxylated alkyl (C12-C22) quaternary surfactant, and an alcohol ethoxylate with less than 10 EO units, and mixtures thereof.

The present invention is also directed to a method for reducing spray drift during the spraying of an aqueous solution. The method comprising: providing a nonionic MEHEC polymer described in the present invention; combining the MEHEC polymer with at least one agricultural chemical to obtain the aqueous solution; and spraying the aqueous solution.

In one aspect of the invention, the volume of fine droplets of <150 microns is reduced by >30% during the spraying of the aqueous solution; in another aspect of the invention, by >35%; in yet another aspect of the invention, by >40%; in one other aspect of the invention, by >50%.

The present invention is also directed to a method for increasing resistance to rain wash off of an aqueous solution sprayed onto a surface. The method comprises: providing a nonionic MEHEC polymer described in the present invention; combining the MEHEC polymer with at least one agricultural chemical to obtain the aqueous solution; and spraying the aqueous solution onto the surface. The surface may be a surface of a plant, e.g., leaf surface.

In one aspect of the invention, the method according to the present invention does not involve the (additional) use of aluminosilicate mineral, particularly foamed aluminosilicate mineral. In another aspect of the invention, the method according to the present invention does not involve the (additional) use of granules with pores.

The present invention will now be illustrated by the following non-limiting examples.

EXAMPLES

Throughout the examples, the droplets refer to the droplets in the spray mist and the concentration is in wt % unless specified.

Example 1: The Viscosity of Different Cellulose Ether Polymers in 1% Water Solutions The different cellulose ether polymers (i.e., EHEC, MEHEC, and HMEHEC) are available from AkzoNobel under the brand name Bermocoll®. In addition, the preparation of MEHEC is described in International Patent Application WO2012/080301 and U.S. Pat. No. 7,319,146, both of which are incorporated by reference herein in their entireties.

2.00 g of the cellulose ether polymers was dispersed in about 50 ml of de-ionized water in a 250 ml glass beaker (height 12 cm, diameter 6.5 cm). The dispersion was kept swirling until lump-free. 50 ml buffer solution of pH=7 was added at ambient temperature followed by the addition of de-ionized water to adjust the total weight of 200 g. The dispersion was then stirred for two hours at 60 rpm and placed in water bath for 1.5 hours at 20° C. before viscosity measurement. Brookfield viscometer type LV was used to measure the viscosity of the 1% solution in the beaker at 12 rpm with Spindle No. 2 (for viscosity between 250 to 3,000) or Spindle No. 3 (for viscosity between 2,500 to 10,000). Table 1 shows the viscosity of different polymers solution at 1% concentration.

TABLE 1

The viscosity of 1% solution of various cellulose ether polymers in water

| Cellulose ether polymers | $MS_{EO}$ | $DS_{ET}$ | $DS_M$ | $DS_H$ | Viscosity, cps |
|---|---|---|---|---|---|
| EHEC 1 | 1.9 | 0.9 | — | — | 400 |
| EHEC 2 | 2.6 | 0.9 | — | — | 5000 |
| HMEHEC 1 | 2.6 | 0.9 | — | 0.01 | 525 |
| HMEHEC 2 | 2.6 | 0.9 | — | 0.01 | 2350 |
| MEHEC 1 | 1.1 | 0.3 | 0.7 | — | 12000 |
| MEHEC 2 | 2.4 | 0.4 | 0.5 | — | 8000 |

Example 2: Effect of Different Cellulose Ether Polymers on Drift Control Performance It is generally agreed that the spray droplet sizes most susceptible to drift are those below about 150 μm. The preferred range of droplet size diameters for commercial aerial sprays lies from about 200 microns to about 400 microns.

The spray droplet distribution measurement was performed using a Sympatec Helos/R laser diffraction particle size analyzer fitted with the R6 lens that is capable of detecting droplets in air from 0.5 μm to 1750 μm. The "% volume<150 μm" is a value describing the percent volume of droplets whose size is below 150 μm.

The spray nozzle used in the experiment was a TEEJET 8002 flat fan nozzle. The studied aqueous solution is ejected out through the nozzle under a pressure of 40 psi N2. The design of this type of nozzle is able to produce a lot of fine droplets. For water, in our spray setup, the typical % volume<150 μm is about 50-55%. Some diluted aqueous pesticide solutions produce more than 48-53% droplets with size<150 μm (measured with Sympatec Helos/R mentioned above). A good drift control agent is defined as one that can reduce the % volume<150 μm by >30%. It is understood that the higher the percentage (e.g., >30%, >40%, >50%), the better the drift control agent is.

During the sample preparation, the different cellulose ether polymers were added to aqueous solution, then the prepared solutions were sprayed at the conditions described above.

A number of formulations were prepared and sprayed both with and without drift control agents. Water was used as reference in the tests because water is the medium and water generates a lot of fine droplets during spraying.

The studied concentration was 0.05 wt % in water or in various herbicide solutions. The solution at this concentration appeared to be slightly more viscous than pure water.

Ag—RHO® DR-2000, which is hydroxypropyl modified guar gum, is used as a positive control because Ag—RHO® DR-2000 is one of the most popular drift control agents used in the current market.

The drift control data is shown in Table 2.

TABLE 2

The drift control performance of 0.05 wt % drift control agents in water

| Products | x50/μm[1] | % <150 μm | % Reduction from water |
|---|---|---|---|
| Water | 155 | 52 | |
| DR-2000 | 204 | 33 | 37 |
| EHEC 1 | 180 | 40 | 23 |

TABLE 2-continued

The drift control performance of 0.05 wt % drift control agents in water

| Products | x50/μm[1] | % <150 μm | % Reduction from water |
|---|---|---|---|
| EHEC 2 | 175 | 41 | 21 |
| HMEHEC 1 | 162 | 46 | 12 |
| HMEHEC 2 | 172 | 43 | 17 |
| MEHEC 1 | 215 | 30 | 42 |
| MEHEC 2 | 206 | 32 | 38 |

[1]x50/μm is the droplet size in μm where 50% of the droplets are below this size.

As shown in Table 2, some of the cellulose ether polymers only reduced slightly the volume of fine droplets by less than 25% while the MEHEC polymers were able to reduce the fine droplets by >~38%. In comparison, the market standard, DR-2000, was able to reduce the fine droplets by 37%.

Example 3: Effect of Herbicides on the Drift Control Property of MEHEC 1

It is well known that pesticide formulations can have significant impact on the performance of drift control agents due to the presence of surfactants in the formulation. To examine the effect of pesticide formulations, MEHEC 1 was added to two of the most commonly used herbicides: glyphosate (from Roundup® WeatherMax) and 2,4-D (2,4-D dimethylamine salt). WeatherMax contains K-glyphosate and some surfactants.

When MEHEC 1 was combined with either 1% ae glyphosate WeatherMax or 1.0% ae 2,4-D DMA, a significant reduction on driftable fine was achieved. The results are shown in Table 3.

TABLE 3

Drift control performance of MEHEC 1 in Roundup WeatherMax and 2,4-D DMA spray solution

| Samples | Average droplet size (μm) | % <150 μm | % Reduction |
|---|---|---|---|
| Water | 145 | 52 | |
| 0.05 wt % MEHEC 1 in water | 205 | 34 | 35 |
| 0.05 wt % MEHEC 1 with 1% ae WeatherMax | 211 | 32 | 38 |
| 0.05 wt % MEHEC 1 with 1% ae 2,4 D | 260 | 27 | 48 |

The results in Table 3 show that MEHEC 1 is robust and it was able to reduce the fine droplets by ~35% in water, ~38% in WeatherMax, and ~48% in 2,4-D DMA. The reduction is more than enough to be considered as an effective drift control agent.

Example 4: Effect of Ammonium Sulfate (AMS) and Glyphosate Formulation on the Drift Control Property of MEHEC 1 and Ag—RHO® DR-2000

Ammonium sulfate (AMS) is widely used together with a glyphosate formulation in North America for better biological effect while spraying glyphosate. The effect of AMS on the drift control property of MEHEC 1 was studied. The results are shown in Table 4.

TABLE 4

Comparison of drift control performance of MEHEC 1 and DR-2000 in 1.0% ae Weather Max and 2 wt % AMS

| Samples | Average droplet size (μm) | % <150 μm | % Reduction |
|---|---|---|---|
| 1.0% ae Weather Max and 2 wt % AMS | 140.0 | 54.9 | |
| 1.0% ae Weather Max and 2 wt % AMS + 0.031 wt % DR-2000 | 171.0 | 43.2 | 21 |
| 1.0% ae Weather Max and 2 wt % AMS + 0.031 wt % MEHEC 1 | 181.0 | 39.7 | 28 |
| 1.0% ae Weather Max and 2 wt % AMS + 0.0625 wt % DR-2000 | 200.0 | 35.1 | 36 |
| 1.0% ae Weather Max and 2 wt % AMS + 0.0625 wt % MEHEC 1 | 188.0 | 38.3 | 30 |

Example 5: Comparison of Drift Control Performance of MEHEC 1 and DR-2000 in 1.0 wt % ae Weather Max, 1% ae 2,4-D DMA Salt, and 2 wt % AMS (Ammonium Sulfate)

In order to achieve the desirable weed control effect, sometimes more than one herbicide is mixed and applied together. The following example shows the drift control property of a mixture of two common herbicides, Roundup® WeatherMax and 2,4-D DMA plus AMS, with MEHEC 1 and DR-2000. The results are shown below in Table 5.

TABLE 5

Comparison of drift control performance of MEHEC 1 and DR-2000 in 1.0 wt % ae Weather Max, 1.0 wt % 2,4-D ae, and 2 wt % AMS

| Samples | Average droplet size (μm) | % <150 μm | % Reduction |
|---|---|---|---|
| 1.0% ae Weather Max + 1.0% 2,4-D ae + 2 wt % AMS | 134 | 57 | |
| 1.0% ae Weather Max + 1.0% 2,4-D ae + 2 wt % AMS + 0.0625 wt % DR-2000 | 173 | 42 | 26 |
| 1.0% ae Weather Max + 1.0% 2,4-D ae + 2 wt % AMS + 0.0625 wt % MEHEC 1 | 172 | 42 | 26 |

Results in Table 5 showed that at 0.0625% use rate, MEHEC 1 performed similarly to the market standard DR-2000 in 1.0% ae Weather Max, 1.0% ae 2,4-D DMA and 2 wt % AMS solution.

Example 6: Rainfastness Assessment

Rainfastness is another desired attribute for agro chemical application. MEHEC 1 solution at a concentration of 0.2 wt % is mixed with a water soluble dye Tartrazine at 1:1 ratio (polymer:Tartrazine). Drops of the mixture are deposited onto a Parafilm serving as a model hydrophobic plant leaf. The Parafilm is mounted over a Petri dish. The deposited drops are then left to dry at room temperature. After the drops have dried up, the Petri dish covered by the Parafilm with dried drops is placed under a "rain source" for 15 seconds. The "rain source" is created by pulling 400 g water rapidly into a vessel with small holes at the bottom. The appearances of deposited dried drops are compared before and after the simulated rain. Rainfastness is determined by visual inspection of the droplets by the naked eye. The result is captured in a photo as shown in the FIGURE. It should be noted that before the simulated rainfall, all of the Parafilms looked like the one shown in (c).

The results indicate that guar gum shows reasonable rainfastness performance as shown in (b). However, MEHEC 1 shows the best performance with all drops completely retained on the surface after the simulated rainfall as shown in (c).

What is claimed is:

1. An agricultural composition comprising at least one agricultural chemical selected from the group consisting of pesticides, growth regulators, micronutrients, fertilizers and combinations thereof and at least one cellulose ether, wherein the cellulose ether is a nonionic methyl ethyl hydroxyethyl cellulose (MEHEC) polymer having a degree of substitution of greater than about 0.3 for methyl, and a degree of substitution of greater than about 0.2 for ethyl, wherein the composition is capable of forming an aqueous spray solution capable of reducing the volume of fine droplets in mist whose size is less than 150 microns during spraying by at least 30% compared to the same aqueous spray solution without the presence the cellulose ether, and wherein the composition is substantially free of aluminosilicate mineral.

2. The agricultural composition of claim 1 wherein the MEHEC polymer has an average molar substitution of ethylene oxide of greater than about 0.8.

3. The agricultural composition of claim 1 wherein the MEHEC polymer has a viscosity of greater than 5000 cps measured at 1% in water at pH=7 using a Brookfield viscometer type LV at 12 rpm using spindle number 3 at 20 degree C. in a container with diameter of 6.5 cm.

4. The agricultural composition of claim 1 wherein the agricultural composition comprises 0.01-0.5 wt % of the MEHEC polymer and more than about 50 wt % of water.

5. The agricultural composition of claim 1 wherein the pesticide is selected from the group consisting of a herbicide, a fungicide, and an insecticide.

6. The agricultural composition of claim 5 wherein the pesticide is a herbicide.

7. The agricultural composition of claim 6 wherein the herbicide is selected from the group consisting of glyphosate, 2,4-D, and dicamba.

* * * * *